United States Patent
Patel et al.

(10) Patent No.: US 9,423,328 B2
(45) Date of Patent: Aug. 23, 2016

(54) APPARATUS AND METHOD FOR TESTING CUSHIONING COMPONENTS

(71) Applicant: NIKE, Inc., Beaverton, OR (US)

(72) Inventors: Mitesh Patel, Hillsboro, OR (US); Bryan Molloseau, Beaverton, OR (US); Scott Rosenberg, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 97 days.

(21) Appl. No.: 14/469,772

(22) Filed: Aug. 27, 2014

(65) Prior Publication Data

US 2016/0061700 A1    Mar. 3, 2016

(51) Int. Cl.
*G01N 3/32* (2006.01)
*G01N 3/08* (2006.01)
(Continued)

(52) U.S. Cl.
CPC *G01N 3/08* (2013.01); *A43B 13/18* (2013.01); *A47C 31/123* (2013.01); *G01N 3/24* (2013.01); *G01N 3/36* (2013.01); *G01N 2203/0019* (2013.01)

(58) Field of Classification Search
CPC ....... A43D 95/14; A43D 999/00; A43D 1/08; A43D 1/00; B29D 35/12; B29K 2075/00; G01N 3/08; G01N 3/36; G01N 3/34; G01N 3/342; G01N 2203/0019; G01N 2203/0246; G01N 3/32; G01N 2203/0226; G01N 15/0826; G01N 2015/086; G01N 33/36; G01N 3/22; G01N 3/40; G01N 3/30; G01M 99/001; G01M 99/00; A47C 31/123; A47C 31/126; A43B 3/0005; G09B 23/32
USPC ............. 73/818, 865.3, 865.6, 172, 774, 781, 73/866.4, 73, 7; 700/283, 301; 340/665
See application file for complete search history.

(56) References Cited

U.S. PATENT DOCUMENTS 3,413,849 A * 12/1968 Janapol ............... G01M 99/001
                                                  73/161
4,130,007 A    12/1978 Hayashi
(Continued)

FOREIGN PATENT DOCUMENTS

WO        2009102929 A1    8/2009

OTHER PUBLICATIONS

Standard Test Methods for Evaluation of Innersprings, Boxsprings, Mattresses or Mattress Sets, Designation F 1566-08, In: Test Methods for Evaluation of Innersprings, Boxsprings, Mattresses or Mattress Sets, Dec. 31, 2008, ASTM International, West Conshohocken, PA XP055214682, DOI: 10.1520/F1566-08, Figure 5, Section 9.

*Primary Examiner* — Lisa Caputo
*Assistant Examiner* — Brandi N Hopkins
(74) *Attorney, Agent, or Firm* — Quinn Law Group, PLLC

(57) ABSTRACT

An apparatus for testing a cushioning component for a body part includes a jig that has a three-dimensional anatomical shape. A base is configured to support the cushioning component. An actuator is operatively connected to at least one of the jig and the base and is activatable to move said one of the jig and the base toward and away from the other of the jig and the base to repeatedly contact the cushioning component and the jig with one another. An electronic controller has a processor that executes a stored algorithm. The algorithm has a test condition substantially equivalent to an expected in-use condition of the cushioning component. The electronic controller activates the actuator to move the jig and/or the base according to the algorithm. A method of testing a cushioning component is implemented.

20 Claims, 9 Drawing Sheets

(51) Int. Cl.
  *A47C 31/12* (2006.01)
  *G01N 3/24* (2006.01)
  *G01N 3/36* (2006.01)
  *A43B 13/18* (2006.01)

(56) References Cited

U.S. PATENT DOCUMENTS

| | | |
|---|---|---|
| 4,183,156 A | 1/1980 | Rudy |
| 4,219,945 A | 9/1980 | Rudy |
| 4,327,572 A | 5/1982 | Pitman et al. |
| 4,432,223 A | 2/1984 | Paquette et al. |
| 4,906,502 A | 3/1990 | Rudy |
| 4,936,029 A | 6/1990 | Rudy |
| 5,042,176 A | 8/1991 | Rudy |
| 5,563,329 A | 10/1996 | Smith et al. |
| 5,641,917 A | 6/1997 | Hurite et al. |
| 5,713,141 A | 2/1998 | Mitchell et al. |
| 5,821,415 A | 10/1998 | Faust et al. |
| 5,952,065 A | 9/1999 | Mitchell et al. |
| 6,013,340 A | 1/2000 | Bonk et al. |
| 6,082,025 A | 7/2000 | Bonk et al. |
| 6,127,026 A | 10/2000 | Bonk et al. |
| 6,203,868 B1 | 3/2001 | Bonk et al. |
| 6,220,088 B1 | 4/2001 | Scales et al. |
| 6,289,743 B1 | 9/2001 | Norton |
| 6,321,465 B1 | 11/2001 | Bonk et al. |
| 6,386,054 B1 | 5/2002 | Jones et al. |
| 6,739,200 B1 | 5/2004 | Norton |
| 6,918,695 B2 | 7/2005 | Polegato Moretti et al. |
| 8,061,060 B2 | 11/2011 | Swigart et al. |
| 2011/0004354 A1* | 1/2011 | Oxeman .............. A47C 31/123 700/283 |
| 2012/0188088 A1* | 7/2012 | Spampinato ............ G01N 3/08 340/665 |
| 2014/0096588 A1* | 4/2014 | Wolkin .................. G01N 3/32 73/12.01 |

* cited by examiner

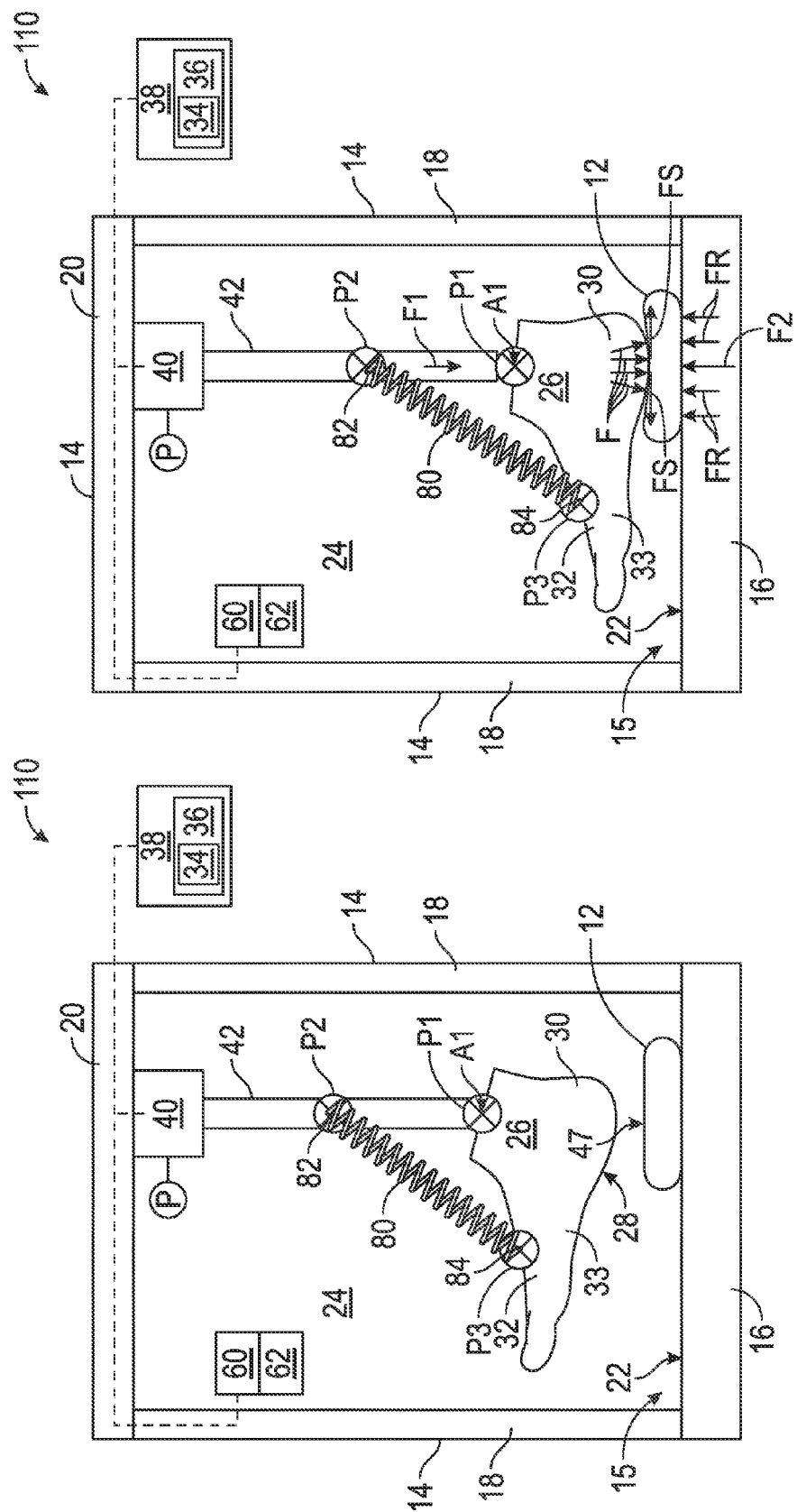

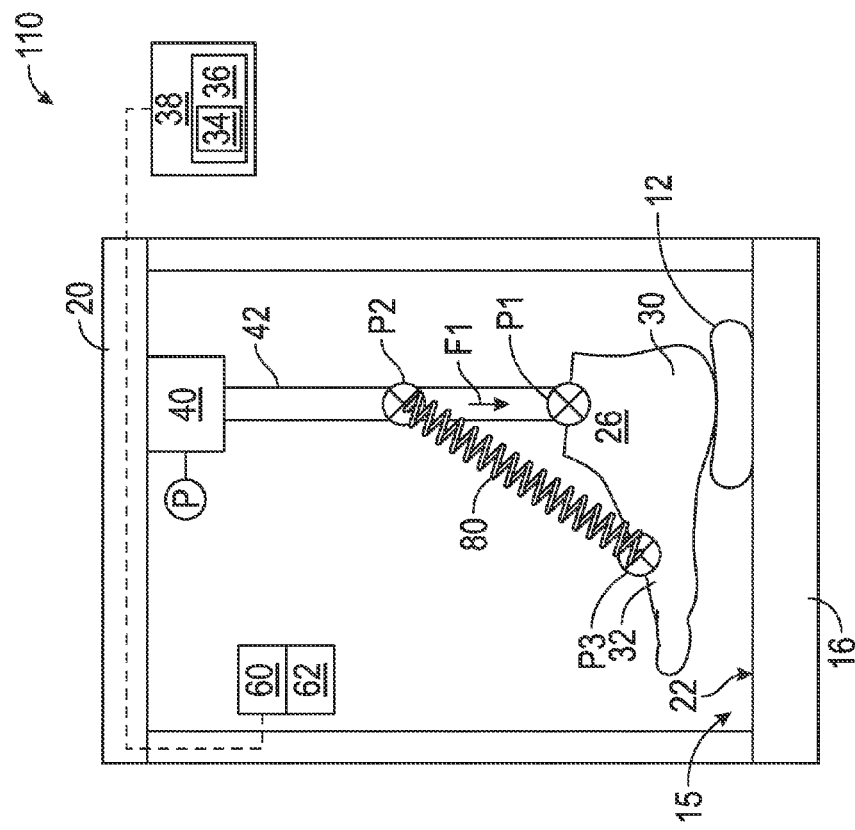
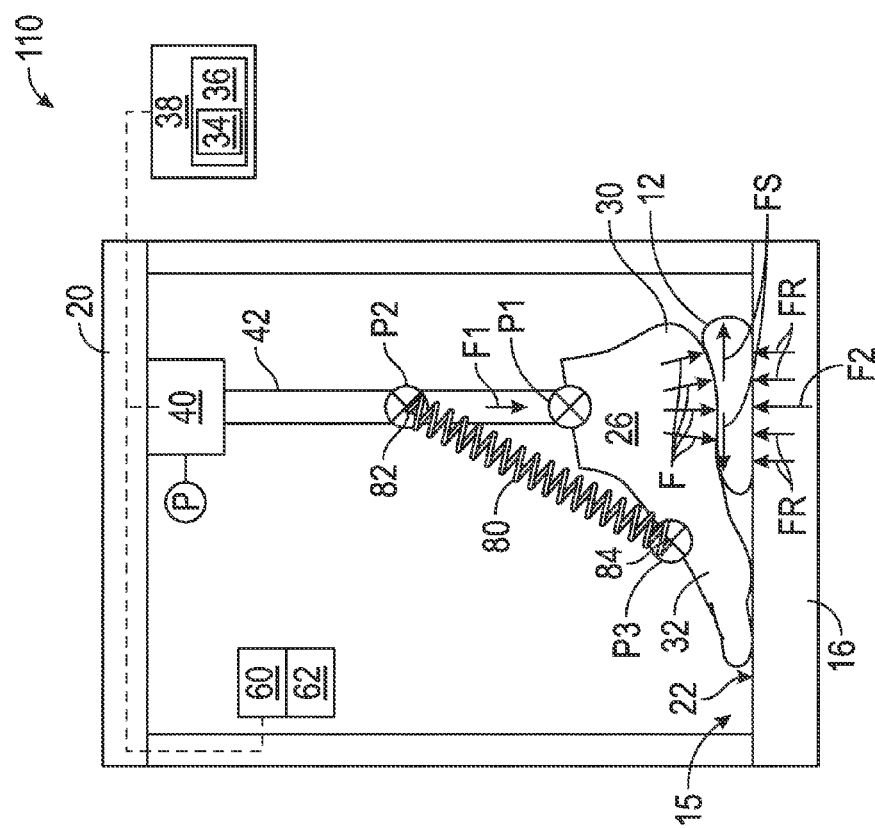

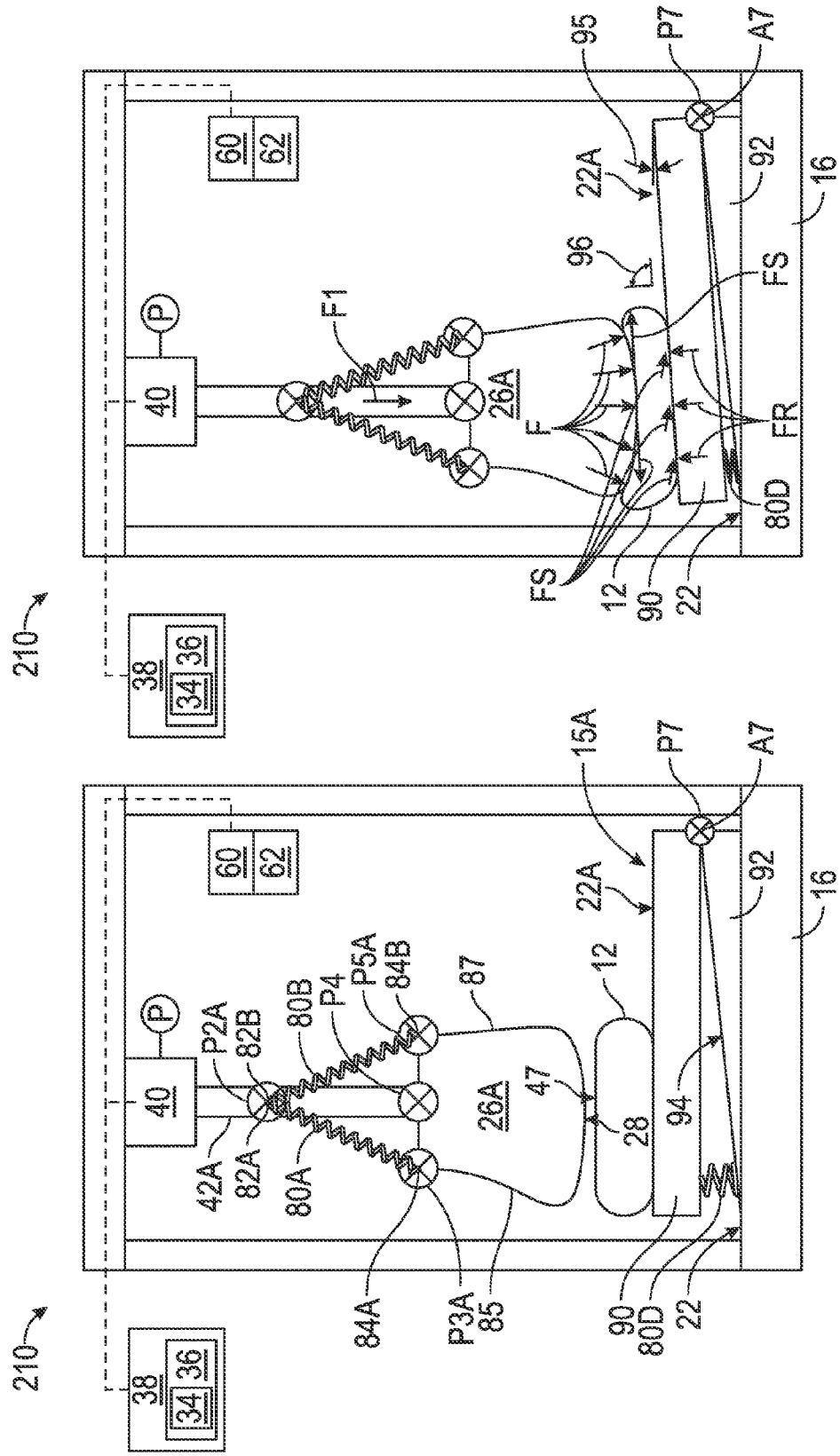

US 9,423,328 B2

APPARATUS AND METHOD FOR TESTING CUSHIONING COMPONENTS

TECHNICAL FIELD

The present disclosure relates to an apparatus and method for testing cushioning components, such as for an article of footwear.

BACKGROUND

Various items can serve as cushioning components for different human body parts. Articles of footwear, athletic apparel, sports equipment, and other components related to athletics often include cushioning components. Furniture and floor mats also have cushioning functions. Manufacturers are interested in ensuring the durability and functioning of these cushioning components throughout their expected useful life, and in testing cushioning components using accurate and efficient methods.

BRIEF DESCRIPTION OF THE DRAWINGS

FIG. 8 is a schematic illustration in side view of a second embodiment of a testing apparatus and a cushioning component, with a pivotable foot-shaped jig spaced from the cushioning component.

FIG. 9 is a schematic illustration in side view of the testing apparatus of FIG. 8, with a heel portion of the pivotable foot-shaped jig beginning compression of the cushioning component.

FIG. 10 is a schematic illustration in side view of the testing apparatus of FIG. 8, with the pivotable foot-shaped jig compressing the cushioning component and pivoted to a second position.

FIG. 11 is a schematic illustration in side view of the testing apparatus of FIG. 8, with a heel portion of the pivotable foot-shaped jig being lifted from the cushioning component.

FIG. 12 is a schematic illustration in rear view of a third embodiment of a testing apparatus with a pivotable base plate in a first position, and with a pivotable foot-shaped jig spaced from a cushioning component.

FIG. 13 is a schematic illustration in rear view of the testing apparatus of FIG. 12, with the pivotable foot-shaped jig compressing the cushioning component and with the base plate pivoted to a second position.

DESCRIPTION

Figure 1:
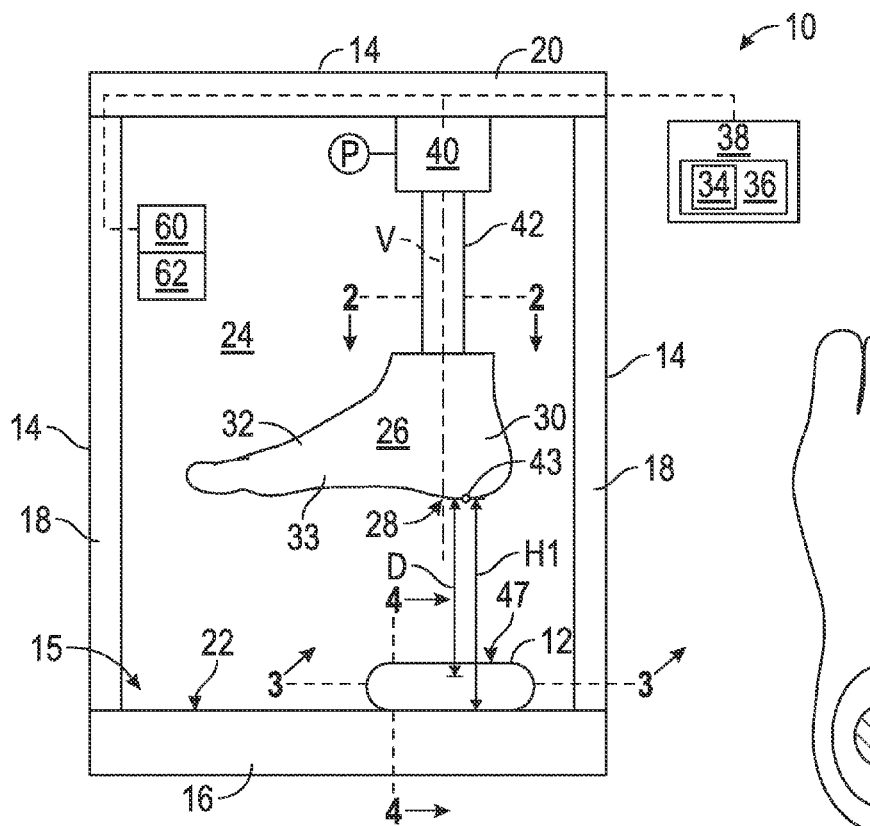
FIG. 1 is a schematic illustration in side view of a first embodiment of a testing apparatus and a cushioning component, with a foot-shaped jig spaced from the cushioning component.

An apparatus for testing a cushioning component includes a jig that has a three-dimensional anatomical shape. A base is configured to support the cushioning component. An actuator is operatively connected to at least one of the jig and the base and is activatable to move at least one of the jig and the base toward and away from the other of the jig and the base to repeatedly contact the cushioning component and the jig with one another. An electronic controller operatively connected to the actuator has a processor that executes a stored algorithm. The algorithm has at least one test condition substantially equivalent to an expected in-use condition of the cushioning component. As used herein, a test condition is "substantially equivalent" to an expected in-use condition if the test condition has a numerical value within ten percent of the numerical value of the expected in-use condition. The electronic controller activates the actuator to move the jig and/or the base according to the algorithm. As used herein, an "in-use" condition is a condition to which the cushioning component would be subjected when used for its intended purpose, such as to cushion an actual human body part, rather than when used during testing with the jig.

In one embodiment, the three-dimensional anatomical shape is a shape substantially identical to a human body part. By way of non-limiting example, the anatomical shape may be any one of a foot shape, a shoulder shape, a knee shape, a hand shape, a head shape, and a buttocks shape. Cushioning components tested by the apparatus may include cushioning components of articles of footwear, such as sole elements, including bladder elements. Other cushioning components may include but are not limited to cushioning in shoulder pads, helmet pads, shin guards, baseball gloves, seat cushions, and floor mats.

In one example, a test condition substantially equivalent to an expected in-use condition may be multi-axial deformation of the cushioning component associated with compressing the cushioning component with the jig. The multi-axial deformation is caused by multi-axial forces of the three-dimensional jig acting on the cushioning component, and results in transverse shear stresses in the cushioning component. The ability of the testing apparatus to replicate multi-axial forces expected in-use ensures that the reliability test to more accurately determine in-use failure modes.

Similarly, another optional test condition substantially equivalent to an in-use condition that may be implemented according to the algorithm may be a number of cycles of compressing the cushioning component with the jig. Still another test condition substantially equivalent to an in-use condition that may be implemented by the algorithm includes a rate of compression of the cushioning component. The actuator can be controlled by the controller to move the jig from an initial height to a final height at the rate of compression. A difference between the initial height and the final height may be a function of at least one of a corresponding foot size of the jig and a predetermined force of application of the jig on the cushioning component.

In an embodiment, the rod may be pivotably connected to the jig and movable by the actuator to move the jig into contact with the cushioning component so that the jig pivots relative to the rod in response to contact with the cushioning component. For example, the anatomical shape of the jig may be a foot shape having a heel portion and a forefoot portion, and the rod may be connected to the jig closer to the heel portion than the forefoot portion. The jig may thus pivot toward the forefoot portion. Pivoting of the jig causes shear forces within the cushioning component during compression by the jig, which shear forces are representative of forces of a pivoting foot acting on the cushioning component.

In an embodiment with a pivotable jig, a biasing member may be connected at a first end to the rod and at a second end to the forefoot portion of the jig. The biasing member may bias the jig to a first position relative to the rod, and the jig may pivot from a first position to a second position relative to the rod upon compression of the cushioning component. The biasing member returns the jig to the first position when the actuator moves the jig away from the base, out of contact with the cushioning component.

In another embodiment, the base includes a pivotable base plate that has a support surface on which the cushioning component is supportable. The pivotable base plate pivots from a first position to a second position upon compression of the cushioning component by the jig. The angle of application of the jig relative to a support surface of the base plate on which the cushioning component is supported is different when the base plate is in the first position than when the base plate is in the second position.

In one embodiment, the base may include an angled plate. The pivotable base plate may be pivotably connected to the angled plate between the jig and the angled plate. The base may include a biasing member operatively connected to at least one of the base plate and the angled plate and biasing the base plate to the first position. With the pivotable base plate and/or the angled plate, the jig will cause shear forces within the cushioning component that are representative of expected in-use shear forces.

In an embodiment in which the rod is pivotably connected to the jig, the anatomical shape of the jig may be a foot shape having a heel portion. The rod may be connected to the jig such that the cushioning component is compressed by the heel portion.

The apparatus may include a first biasing member connecting the rod to a first side of the jig, such as a lateral side of the jig, and a second biasing member connecting the rod to a second side of the jig, such as a medial side of the jig. The jig is thereby pivotable relative to the rod toward either the medial side or the lateral side, from an unpivoted position to a pivoted position, in response to contact with the cushioning component and pivoting of the base plate when the jig compresses the cushioning component. The biasing members may return the jig to the unpivoted position when the jig is moved out of contact with the cushioning component.

In one embodiment, the apparatus can be configured to control a climate condition of an environment of the cushioning component during testing. For example, a frame may support the jig and at least partially surround the jig and the base to define an internal space. A climate control element may be operatively connected to one of the frame and the base. A gauge may be operable to measure a climate condition may be operatively connected to the climate control element. The climate control element and the gauge are both operatively connected to the controller. A test condition carried out by the algorithm may be a predetermined level of the climate condition. The stored algorithm may maintain the internal space at the predetermined level of the climate condition by controlling the climate control element. The climate condition may be a temperature or humidity of the internal space.

A method of testing cushioning components may include moving at least one of a three-dimensional, anatomically-shaped jig and a base toward and away from the other of the jig and the base to repeatedly contact the jig and a cushioning component supported on the base with one another. Moving the jig and/or the base may be by executing an algorithm stored in a processor of an electronic controller to activate an actuator that moves the jig and/or the base. In one example, moving the jig toward the base is by a predetermined distance to compress the cushioning component with the jig. The stored algorithm is a first reliability test having at least one test condition substantially equivalent to an expected in-use condition of the cushioning component. In one example, the algorithm may be executed by the controller until the occurrence of a failure mode of the cushioning component. The specific failure mode may be accelerated by the test condition.

A test condition of the first reliability test may include multi-axial forces acting on the cushioning component and associated with multi-axial deformation of the cushioning component by the jig. Another test condition of the first reliability test may include a rate of compression of the cushioning component, with the jig moving from an initial height to a final height at the rate of compression. Still another test condition may be a number of cycles of compressing the cushioning component with the jig. Additionally or alternatively, the test condition may include a depth of compression of the cushioning component by the jig. The depth of compression is a function of at least one of a corresponding foot size of the jig and a predetermined force of application of the jig on the cushioning component. Another test condition may be a predetermined level of a climate condition of an environment of the cushioning component. In this instance, the method may include controlling the environment of the cushioning component to the predetermined level of the climate condition.

By configuring the apparatus and the method so that the cushioning components are tested with one or more test conditions substantially equivalent to expected in-use conditions, test results for reliability of the cushioning components will be more accurate. Additionally, testing may be carried out more quickly, as failure modes related to in-use conditions can be achieved more quickly. For example, an identified failure mode of the cushioning component caused at least partially by the test condition, such as failure under repeated shear forces, can be replicated.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, a disclosure of a range is to be understood as specifically disclosing all values and further divided ranges within the range.

The terms "comprising," "including," and "having" are inclusive and therefore specify the presence of stated features, steps, operations, elements, or components, but do not preclude the presence or addition of one or more other features, steps, operations, elements, or components. Orders of steps, processes, and operations may be altered when possible, and additional or alternative steps may be employed. As used in this specification, the term "or" includes any one and all combinations of the associated listed items. The term "any of" is understood to include any possible combination of referenced items, including "any one of" the referenced items. The term "any of" is understood to include any possible combination of referenced claims of the appended claims, including "any one of" the referenced claims.

Those having ordinary skill in the art will recognize that terms such as "above," "below," "upward," "downward," "top," "bottom," etc., are used descriptively for the figures, and do not represent limitations on the scope of the invention, as defined by the claims.

The above features and advantages and other features and advantages of the present disclosure are readily apparent from the following detailed description of the best modes for carrying out the concepts of the disclosure when taken in connection with the accompanying drawings.

Referring to the drawings, wherein like reference numbers refer to like components throughout the several views, FIG. 1 is an apparatus 10 for reliability testing of a cushioning component 12 for cushioning a body part. The apparatus 10 has a frame 14 and a base 15 that includes a base member 16. As shown, the frame 14 is a supportive structure with sides 18 and an upper wall 20. The sides 18 support the upper wall 20 above the base 15. Two sides 18 are shown, and these may be walls extending along corresponding sides of the base member 16, or narrower posts situated near corners of the base member 16. The base member 16 may be rectangular, square, or otherwise shaped. If the sides 18 are in the form of posts, multiple additional sides may be placed at the remaining corners of the base member 16. The base member 16 has an upward-facing support surface 22. The frame 14 and base member 16 generally define and bound an internal space 24 serving as an environment of the cushioning component 12. The internal space 24 may be enclosed by the frame 14, or may be open to the environment surrounding the frame 14. Alternatively, additional sides 18 in front and back of the base member 16 in the view of FIG. 1 could be added to selectively enclose the internal space 24.

Figure 2:
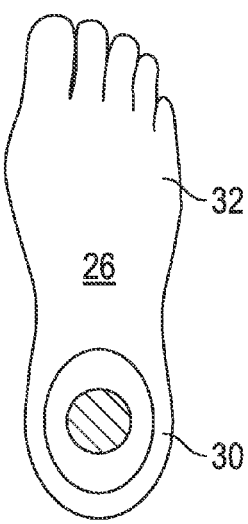
FIG. 2 is a schematic illustration in partially cross-sectional plan view of a jig and rod included in the testing apparatus of FIG. 1, taken at lines 2-2 in FIG. 1.

The apparatus 10 includes a jig 26 supported by the frame 14. The jig 26 is used to compress the cushioning component 12 as described herein. The jig 26 has a three-dimensional anatomical shape substantially identical to a representative body part shape. In the embodiment of FIG. 1, the jig 26 has a three-dimensional anatomical shape of a human foot substantially identical to a human foot of a size corresponding to a shoe size that would contain the cushioning component 12. FIG. 2 shows a plan view of the jig 26, further illustrating the anatomical shape representative of a human foot. The jig 26 has a three-dimensional contoured outer surface 28. The jig 26 is positioned so that the surface 28 at a heel portion 30 of the jig 26 will contact the cushioning component 12 during testing, as described herein. The jig 26 also has a forefoot portion 32. The specific cushioning component 12 tested contacts only the heel portion 30 in the embodiment of FIG. 1. In other embodiments, the cushioning component 12 could extend so that the forefoot portion 32 would also contact the cushioning component during testing. In still other embodiments, the cushioning component 12 could be designed for cushioning a different portion of the human foot, and so may be positioned on the surface 22 to contact only the forefoot portion 32, or some other portion of the jig 26.

The jig 26 is movable into and out of contact with the cushioning component 12 according to a reliability test method, at least a portion of which is represented as an algorithm 34 stored on and executed by a processor 36 of an electronic controller 38 that is operatively connected to the jig 26. More specifically, the electronic controller 38 controls an actuator 40 that is activatable to move the jig 26 relative to the base 16 and the cushioning component 12 supported thereon. For example, the actuator 40 may be activatable by an electronic signal from the controller 38 that causes the actuator 40 to move a rod 42 or other connecting element connecting the actuator 40 to the jig 26. For example, the rod 42 could be a telescoping or otherwise extensible rod that extends in response to the actuator 40. The actuator 40 may be hydraulic, pneumatic, may be an electric motor, or may be any other suitable actuating mechanism. For example, if the actuator 40 is hydraulically actuated, it may include a hydraulic control valve, and the control signal from the controller 38 may move the valve to allow pressurized hydraulic fluid P to act on the rod 42. The rod 42 may be telescopic, such that its length can be varied by the actuator 40. In the embodiment shown, the rod 42 is actuated to extend and retract along an axis V coincident with a longitudinal center axis of the rod 42. Alternatively or in addition, the controller 38 and actuator 40 could be operatively connected to the base member 16 to move the base member 16 toward and away from the jig 26, and the jig 26 could be stationary or, actuators could be operatively connected to both the base member 16 and the jig 26 so that both move toward and away from one another.

Figure 5:
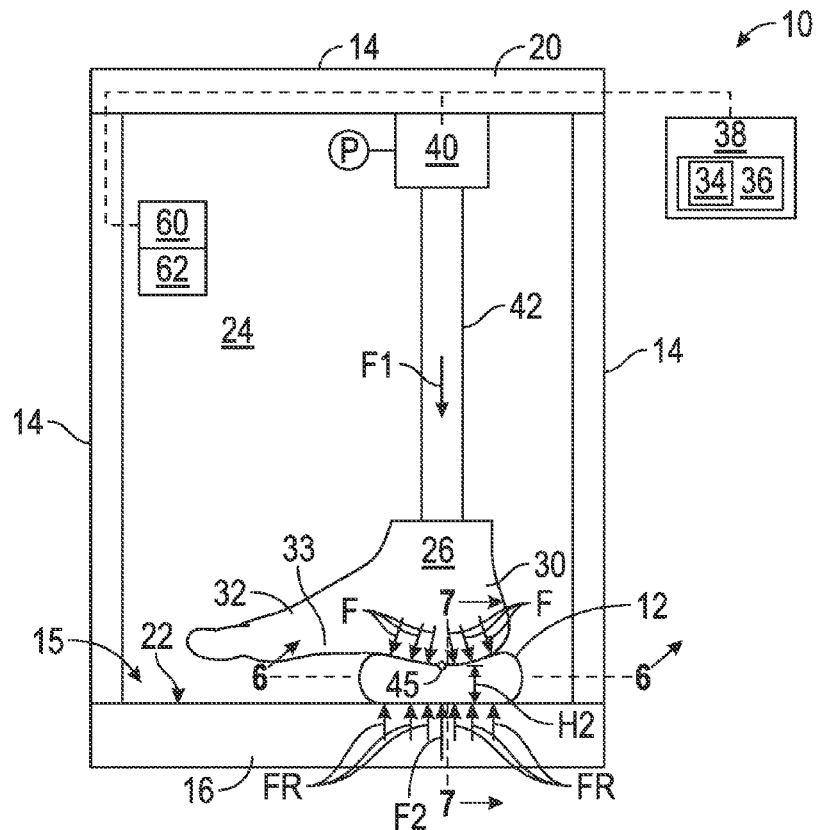
FIG. 5 is a schematic illustration in side view of the testing apparatus and the cushioning component of FIG. 1, with the jig compressing the cushioning component.

The stored algorithm 34 is a first reliability test of the cushioning component 12 and has at least one test condition substantially equivalent to an expected in-use condition of the cushioning component 12. For example, the test condition may be multi-axial deformation of the cushioning component 12 causing multi-axial transverse shear forces to occur in the cushioning component 12. The shear forces may be associated with a portion of the algorithm 34 in which the jig 26 is moved a predetermined distance toward the cushioning component 12 to compress the cushioning component 12. FIG. 5 shows the jig 26 compressing the cushioning component 12 after having been moved by the actuator a predetermined distance D from an initial height H1 at a first position 43 in FIG. 1 to a final height H2 or second position 45 in FIG. 5. The initial height H1 and final height H2 may be measured from a lowest extent of the jig 26 to the surface 22. Because the jig 26 has a three-dimensional anatomical shape of a foot, the surface 28 that will contact an upper surface 47 of the cushioning component 12 will cause multi-axial stresses in the cushioning component 12 that are substantially representative of the multi-axial stresses that will be caused in use, when the cushioning component 12 is included in an article of footwear worn on a human foot.

Figure 3:
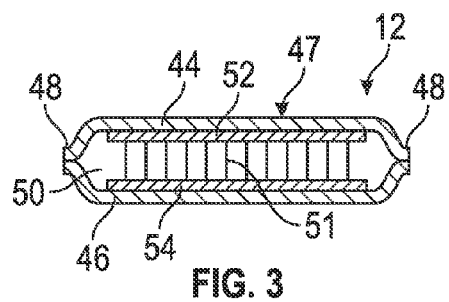
FIG. 3 is a schematic illustration in cross-sectional view of an uncompressed cushioning component to be tested by the apparatus of FIG. 1, taken at lines 3-3 in FIG. 1.
Figure 6:
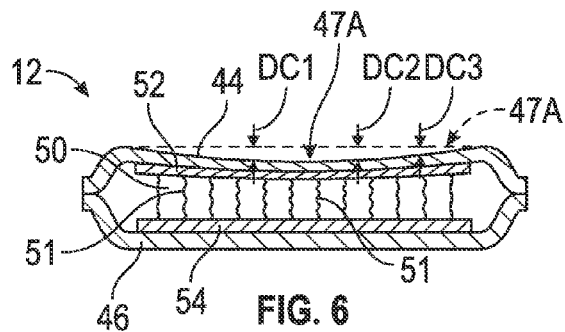
FIG. 6 is a schematic illustration in cross-sectional view of the compressed cushioning component of FIG. 5, taken at lines 6-6 in FIG. 5.
Figure 7:
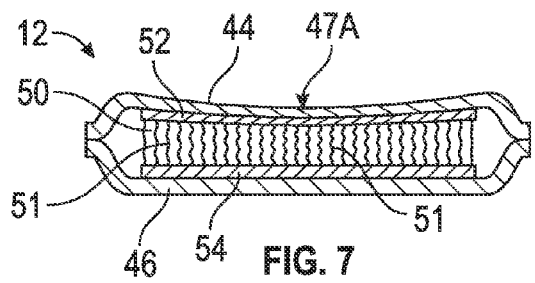
FIG. 7 is a schematic illustration in cross-sectional view of the compressed cushioning component of FIG. 5, taken at lines 7-7 in FIG. 5.

When compressed, the upper surface 47 moves from a generally flat orientation in FIGS. 1 and 3 to a complex-concave shape shown in FIGS. 5-7 and indicated by 47A, consistent with the surface 28 of the jig 26 and the downward force of application F1 of the jig 26. An equal and opposite ground reaction force F2 acts on an outer surface of the lower sheet 46 and is distributed over the outer surface of the lower sheet as forces FR. The force F1 is distributed over the surface of the cushioning component 12 in contact with the surface 28 of the jig 26. Because the cushioning component 12 experiences multi-axial deformation, the force F1 is distributed over the contact surface 47A as multi-axial forces F normal to the surface 47A shown in FIG. 5. The ground reaction force F2 is likewise distributed over the surface of the cushioning component 12 in contact with the surface 22 of the base member 16 as forces FR. The depth of compression of the cushioning component 12 varies across the surface 47, and can be measured by comparing the change in position in a vertical direction of any point on the surface 47 from the position when uncompressed to the compressed position on the compressed surface 47A. For example, three different depths of compression DC1, DC2, DC3 at various locations of the cushioning component 12 are indicated in FIG. 6.

When the jig 26 is the anatomically foot-shaped jig shown, the cushioning component 12 may be any cushioning component used in an article of footwear, such as any sole element, channel fabric, mechanical spring, or liquid medium. In the embodiment shown, the cushioning component 12 is a bladder element for an article of footwear. More specifically, in the embodiment shown, the cushioning component 12 is a fluid-filled bladder element that is configured to lie under the corresponding heel portion 30 of the jig 26 and under the heel portion of a human foot when the cushioning component 12 is included in a sole structure of an article of footwear. As used herein "fluid" filling the bladder element may be air or another gas or combination thereof. The bladder element can be supported by and secured to one or more midsole or outsole layers of the article of footwear. In other embodiments, the cushioning component 12 could be a full-length bladder element, so that it is configured to lay under the forefoot portion 32 and midfoot portion 33 of the jig 26 and of a human foot as well.

Figure 4:
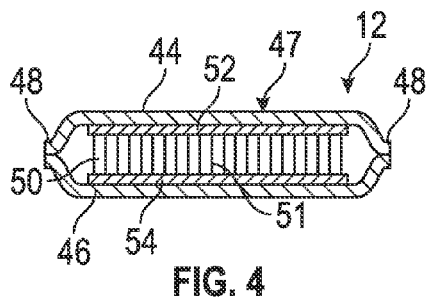
FIG. 4 is a schematic illustration in cross-sectional view of an uncompressed cushioning component tested by the apparatus of FIG. 1, taken at lines 4-4 in FIG. 1.

Referring to FIGS. 3 and 4, the cushioning component 12 may be thermoformed in a mold assembly from an upper sheet 44 and a lower sheet 46. Once thermoformed, the sheets 44, 46 are bonded to one another at a peripheral flange 48 to form a fluid-filled internal cavity 50 therebetween. The cushioning component 12 can be formed from a variety of polymeric materials that can resiliently retain a fluid such as nitrogen, air, or another gas. Examples of polymeric materials for the cushioning component 12 include thermoplastic urethane, polyurethane, polyester, polyester polyurethane, and polyether polyurethane. Moreover, the cushioning component 12 can be formed of layers of different materials including polymeric materials. In one embodiment, the cushioning component 12 is formed from thin films having one or more thermoplastic polyurethane layers with one or more barrier layers of a copolymer of ethylene and vinyl alcohol (EVOH) that is impermeable to the pressurized fluid contained therein as disclosed in U.S. Pat. No. 6,082,025, which is incorporated by reference in its entirety. The barrier layer may include an ethylene-vinyl alcohol copolymer that is impermeable to a fluid within the cavity 50, such that the fluid cannot pass through the barrier layer and is retained within the cavity 50.

In one embodiment, the barrier layer can be a laminate membrane having alternating layers of thermoplastic polyurethane and layers of an ethylene-vinyl alcohol copolymer. The cushioning component 12 may also be formed from a material that includes alternating layers of thermoplastic polyurethane and ethylene-vinyl alcohol copolymer, as disclosed in U.S. Pat. Nos. 5,713,141 and 5,952,065 to Mitchell et al. which are incorporated by reference in their entireties. Alternatively, the layers may include ethylene-vinyl alcohol copolymer, thermoplastic polyurethane, and a regrind material of the ethylene-vinyl alcohol copolymer and thermoplastic polyurethane. The cushioning component 12 may also be a flexible microlayer membrane that includes alternating layers of a gas barrier material and an elastomeric material, as disclosed in U.S. Pat. Nos. 6,082,025 and 6,127,026 to Bonk et al. which are incorporated by reference in their entireties. Additional suitable materials for the cushioning component 12 are disclosed in U.S. Pat. Nos. 4,183,156 and 4,219,945 to Rudy which are incorporated by reference in their entireties. Further suitable materials for the cushioning component 12 include thermoplastic films containing a crystalline material, as disclosed in U.S. Pat. Nos. 4,936,029 and 5,042,176 to Rudy, and polyurethane including a polyester polyol, as disclosed in U.S. Pat. Nos. 6,013,340, 6,203,868, and 6,321,465 to Bonk et al. which are incorporated by reference in their entireties. In selecting materials for the cushioning component 12, engineering properties such as tensile strength, stretch properties, fatigue characteristics, dynamic modulus, and loss tangent can be considered. The thicknesses of sheets of materials used to form the cushioning component 12 can be selected to provide these characteristics.

The cushioning component 12 is resilient and provides cushioning and flexibility that can be tuned such as by selecting a level of pressurization. Tensile members and/or reinforcing structures can be integrated with the cushioning component 12 to provide desired responsiveness, such as disclosed in U.S. Pat. No. 4,906,502 to Rudy et al., and U.S. Pat. No. 8,061,060 to Swigart et al., which are incorporated by reference in their entireties.

In the embodiment of FIGS. 1-7, the cushioning component 12 has fabric tensile members in the form of drop threads 51 connecting a first fabric layer 52 to a second fabric layer 54. The fabric layers 52, 54 are bonded to internal surfaces of the respective sheets 44, 46. The threads 51 restrain separation of the sheets 44, 46 to the maximum separated positions shown in FIGS. 3 and 4 under a given inflation pressure of the cushioning component 12, and yet do not present resistance to compression or any cushioning function when under a compressive load.

When pressure is exerted on the sheets 44, 46 due to a wearer's weight or due to application of the jig 26, the sheets 44, 46 are compressed and move closer together, as illustrated in FIGS. 6 and 7. The threads 51 collapse in proportion to the pressure exerted on the sheets 44, 46 adjacent the threads 51, and the varying depth of compression of the cushioning component 12. Because of the contoured surface 28 of the jig 26 and resulting multi-axial deformation of the cushioning component 12, the forces F exerted on the cushioning component 12 extend in multiple directions and may be referred to as multi-axial forces. In other words, the forces are not uniaxial or evenly applied to the cushioning component 12, so portions of the cushioning component 12 are more compressed than others, and the threads 51 do not collapse uniformly. In-use, a human foot will compress the cushioning component 12 in this non-uniform manner, applying multi-axial forces thereon. The three-dimensional anatomically-shaped jig 26 thus enables reliability testing of the cushioning component 12 to more accurately mimic in-use conditions than would a reliability test having a flat, uncontoured surface contacting the component 12 causing uniaxial deformation of the cushioning component 12, or even a contoured surface that is not anatomically shaped acting on the cushioning component 12. Any damping forces of the cushioning component 12 affect the depth of compression and speed of compression.

In addition to the use of the three-dimensional anatomically-shaped jig 26 as a test condition substantially equivalent to an expected in-use condition (i.e., compression by a corresponding three-dimensional human foot), the stored algorithm 34 may include one or more additional test conditions that are substantially equivalent to an expected in-use condition. For example, the stored algorithm 34 may include moving the jig 26 to repeatedly contact and withdraw from contact the surface 28 of the jig and the surface 47 of the cushioning component 12. The cyclical contact can cause repeated compression of the cushioning component 12, which may be at consistent or varying forces in the cycles. The cyclic compression may be designed to replicate in-use cyclic loading of the cushioning component 12 when included in an article of footwear worn on a human foot. One test condition may be a predetermined number of cycles of compressing the cushioning component 12 with the jig 26.

The stored algorithm 34 may include a predetermined depth of compression of the cushioning component. In other words, the actuator 40 can be controlled by the controller 38 to move the jig 26 from the initial height H1 at the first position 43 to the final height H2 at the second position 45 to result in a predetermined depth of compression DC2 of the cushioning component 12, where the depth of compression varies over the cushioning component 12, as illustrated with depths of compression DC1, DC2, DC3 in FIG. 6. The predetermined depth of compression may be the maximum depth of compression of any portion of the cushioning component 12, such as the maximum depth of compression, DC2 shown in FIG. 6.

A predetermined, controlled rate of compression of the cushioning component 12 may be another test condition included in the stored algorithm 34. In other words, the actuator 40 can be controlled by the controller 38 to move the jig 26 from an initial height H1 at the first position 43 to a final height H2 at the second position 45 at a predetermined speed that results in the predetermined rate of compression of the cushioning component 12. Where the depth of compression varies over the cushioning component 12, as illustrated with depths of compression DC1, DC2, DC3 in FIG. 6, the rate of compression will also vary dependent upon the specific location on the cushioning component 12. Accordingly, the predetermined rate of compression controlled according to the algorithm 34 may be the maximum rate of compression of any portion of the cushioning component 12, which will correspond with the maximum depth of compression, such as at DC2.

Optionally, any or all of the maximum depth of compression DC2, the maximum predetermined rate of compression, the predetermined distance D that the jig 26 is moved or a difference between the initial height H1 and the final height H2 can be controlled under the algorithm 34 to be a function of at least one of a shoe size corresponding to the size of the jig 26 and a predetermined force of application F1 of the jig 26 on the cushioning component 12. One non-limiting example the final height H2 can correspond to the expected height of the jig 26 when representing compression of the cushioning component 12 by a size 11 human foot and a 250 pound person, with the force of application F1 being three times the body weight of the person. The controller 38 can thus control the movement of the rod 42 by the actuator 40, and the pressure applied to the actuator 40 to move the rod 42 according to a stored look-up table of shoe size, body weight, and corresponding applied force.

In addition, expected in-use environmental conditions, such as temperature or humidity can be a controlled test condition of the first reliability test stored as the algorithm 34. The apparatus 10 may include a climate control element 60 and a gauge 62, both of which are operatively connected to the controller 38. The climate control element 60 and the gauge 62 may be connected to and supported by the frame 14 or the base member 16 and in communication with the internal space 24. The climate control element 60 may be a heating element, or a cooling element, and the gauge 62 may be a temperature gauge operable to measure the temperature of the internal space 24. Alternatively or in addition, the climate control element 60 may be a humidifier, and the gauge 62 may be operable to be measure the humidity of the internal space 24. One test condition that may be included in the stored algorithm can thus be a predetermined temperature level, and the stored algorithm 34 can include heating the internal space 24 to at least the predetermined temperature level, such as a temperature of 120 degrees Fahrenheit or less, or cooling the internal space 24 to at least a predetermined temperature level, such as −15 degrees Fahrenheit by control of the climate control element 60. Another test condition that can be included in the stored algorithm 34 can thus be a predetermined humidity level of the internal space 24.

The first reliability test carried out by the controller 38 according to the stored algorithm 34 can be used to determine a failure mode of the cushioning component 12 when subjected to the test conditions of the first reliability test. For example, the cushioning component 12 may be determined to fail under the first reliability test if it achieves a depth of compression greater than a threshold depth of compression. The first reliability test may indicate that this occurs when a test condition is at a first testing parameter, such as when the predetermined force F1 is at a first force level, and is applied a first number of times by a first test time. To expedite testing of cushioning components, the knowledge gained from the first reliability test can be used to modify the stored algorithm 34 in order to shorten the test time. For example, the stored algorithm 34 can be modified to carry out a second reliability test different from the first reliability test in that the predetermined force F1 is applied to the next tested cushioning component 12 the first number of times by a second test time earlier than the first test time. The failure mode of the cushioning component 12 should thus occur earlier in the second reliability test than in the first reliability test.

Figure 20:
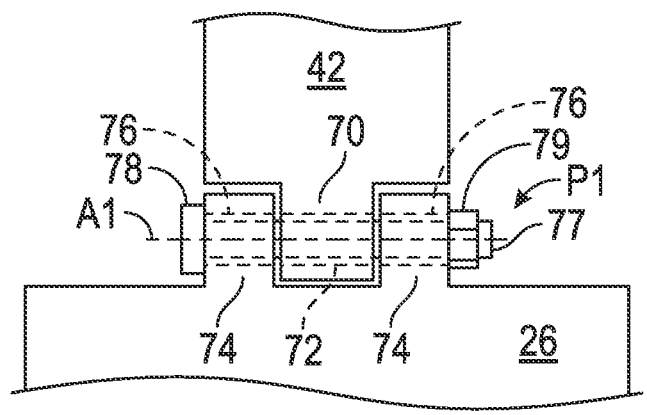
FIG. 20 is a schematic fragmentary illustration of a pivot connection included in the apparatus of FIG. 8.

FIGS. 8-11 show another embodiment of an apparatus 110 for testing a cushioning component, such as cushioning component 12. The apparatus 110 includes many of the same components as shown and described with respect to FIGS. 1-7, as identified with like reference numbers. The apparatus 110 includes a first pivot connection P1 connecting the rod 42 to the jig 26. The first pivot connection P1 may be any suitable connection joining the rod 42 to the jig 26 in a pivotable arrangement. FIG. 20 shows one example pivot connection P1 in which the rod 42 has a center knuckle 70 with an internal opening 72. The jig 26 has a pair of spaced knuckles 74, each with an internal opening 76. The knuckle 70 fits between the knuckles 74 so that the internal opening 72 aligns with the openings 76. A hinge pin 77 is then inserted through the aligned openings 72, 76. A head 78 of the hinge pin 77 larger than the opening 76 is at one side of the aligned knuckles 70, 74 and a nut 79 is threaded to the hinge pin 77 at the other side of the aligned knuckles 70, 74. A center longitudinal axis A1 of the hinge pin 77 defines a pivot axis of the pivot connection P1.

Because of the pivot connection P1, the jig 26 pivots relative to the rod 42 in response to contact with the cushioning component 12 when compressing the cushioning component 12. The distribution of the force F1 as multi-axial forces F over the contact surface 47 of the cushioning component 12 and the reaction forces acting on the jig 26 cause the jig 26 to pivot forward, counter-clockwise in the view of FIGS. 8-11, when the rod 42 presses the jig 26 downward. The forefoot portion 32 of the jig 26 thus moves downward into contact with the surface 22 of the base member 16, as shown in moving from the position in FIG. 8 to the position in FIG. 9, and then to the position in FIG. 10.

FIG. 8 shows a biasing member 80, such as a coil spring, connected at a first end 82 to the rod 42 and is connected at a second end 84 to a forefoot portion 32 of the jig 26. Pivot axis P2 of the biasing member 80 relative to the rod 42 and pivot axis P3 of the biasing member 80 relative to the jig 26 established by the connection of the biasing member 80 to the rod 42 and to the jig 26 at the ends 82, 84, respectively. The biasing member 80 biases the jig 26 to the first position of FIG. 8 relative to the rod 42. The first position of FIG. 8 may also be referred to as an unpivoted position. The jig 26 pivots relative to the rod 42 from the first position of FIG. 8, through the position of FIG. 9, and to a second position of FIG. 10 upon compression of the cushioning component 12. The second position of FIG. 10 may also be referred to as a pivoted position. The biasing member 80 is placed in tension when the jig 26 pivots to the position of FIG. 10. The reaction forces acting on the jig 26 by contact with the cushioning component 12 are greater than the biasing force of the biasing element 80, so that the jig 26 will pivot. The reaction forces acting on the three-dimensional surface 28 of the jig 26 cause pivoting of the jig 26 in the counter-clockwise direction. Accordingly, when the force F1 applied by the rod 42 is released and the actuator 40 moves the jig 26 away from the base member 16 out of contact with the cushioning component 12, the biasing member 80 returns the jig 26 to the first position of FIG. 8 by causing the jig 26 to rotate clockwise about the pivot connection P1. Movement of the jig 26 back toward the first position of FIG. 8 is indicated in FIG. 11. In other embodiments, the biasing member 80 could be another resilient member, or a hydraulic or pneumatic piston instead of a coil spring.

The pivoting of the jig 26 upon contact with and compression of the cushioning component 12 will cause the distributed forces F acting on the cushioning component 12 via the three-dimensional surface 28 of the jig 26 to more realistically reflect expected in-use conditions. For example, a human foot with a shoe thereon often strikes the ground at a heel region of the shoe and pivots from the heel region to the forefoot region during forward movement. This creates transverse shear forces $F_s$ within the cushioning component 12. By more closely replicating the expected in-use conditions, the algorithm 34 carried out by the controller 38 can more accurately test for and identify failure modes of the cushioning component 12.

Figure 21:
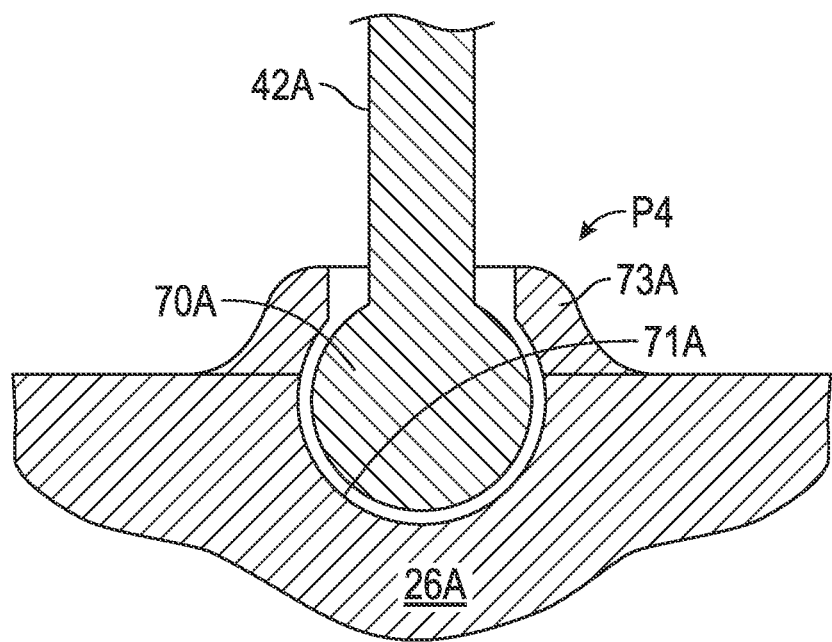
FIG. 21 is a schematic fragmentary cross-sectional illustration of a pivot connection included in the apparatus of FIG. 12.

FIGS. 12-13 show another embodiment of an apparatus 210 for testing a cushioning component, such as cushioning component 12. The apparatus 210 includes many of the same components as shown and described with respect to FIGS. 1-11, as identified with like reference numbers. The apparatus 210 includes a first pivot connection P4 connecting a rod 42A to a jig 26A. The first pivot connection P4 may be any suitable connection joining the rod 42A to the jig 26A in a pivotable arrangement. The rod 42A and the jig 26A function as described with respect to rod 42 and jig 26, and are different only in the area of the first pivot connection P4. Specifically, the rod 42A and jig 26A are configured to establish a ball joint as the first pivot connection P4. With reference to FIG. 21, the rod 42A has a rounded end 70A that is captured in a rounded cavity 71A of the jig 26A. The rounded end 70A may be press-fit into the cavity 71A, or the jig 26A may have an annular cap 73A secured to the body of the jig 26A with screws or other fasteners (not shown) to capture the rounded end 70A after insertion in the cavity 71A. Alternatively, the first pivot connection P4 may be a single axis pivot similar to pivot connection P1 of FIG. 20 but positioned to allow pivoting of the jig 26A relative to the rod 42A in a counter-clockwise direction as viewed in FIG. 12 (toward a lateral side 85 of the jig 26A) or in a clockwise direction as viewed in FIG. 12 (toward a medial side 87 of the jig 26A).

The apparatus 210 further includes a first biasing member 80A pivotably connecting the rod 42A to the lateral side 85 of the jig 26A, also referred to herein as a first side of the jig 26A. The first biasing member 80A may be a coil spring, and is connected at a first end 82A to the rod 42A and is connected at a second end 84A to the lateral side 85 of the jig 26A. Pivot axes P2A, P3A of the biasing element 80A relative to the rod 42A and the jig 26A, respectively, are established by the connection of the biasing element 80A to the rod 42A and to the jig 26A at the ends 82A, 84A.

A second biasing member 80B pivotably connects the rod 42A to the medial side 87 of the jig 26A, also referred to herein as a second side of the jig 26A. The second biasing member 80B may be a coil spring, and is connected at a first end 82B to the rod 42A and is connected at a second end 84B to the medial side 87 of the jig 26A. Pivot axes P2A, P5A of the biasing element 80B relative to the rod 42A and the jig 26A, respectively, are established by the connection of the biasing element 80B to the rod 42A and to the jig 26A at the ends 82B, 84B, respectively.

With the pivot connection P4 and the biasing members 80A, 80B connecting the jig 26A to the rod 42A in this manner, the jig 26A is pivotable relative to the rod 42A toward either the lateral side 85 or the medial side 87 in response to the three-dimensional contoured outer surface 28 of the jig 26A contacting and compressing the surface 47 of the cushioning component 12. For example, the jig 26A is shown slightly pivoted relative to the rod 26A in moving from the first position of FIG. 12 to the second position of FIG. 13. The biasing members 80A, 80B bias the jig 26A to the first position of FIG. 12 relative to the rod 42A. Accordingly, when the jig 26A is withdrawn from contact with the cushioning component 12 upon the actuator 40 moving of the rod 42A in an upward direction in FIG. 12, the jig 26A returns to the first position of FIG. 12.

The apparatus 210 of FIGS. 12-13 has a base 15A that includes a pivotable base plate 90 having a support surface 22A on which the cushioning component 12 is supported. The base 15A further includes an angled plate 92 supported on the base member 16. The angled plate 92 has an upper surface 94 arranged at an angle to the surface 22 of the base member 16. The pivotable base plate 90 is pivotably connected to the angled plate 92 between the jig 26A and the angled plate 92 at a pivot connection P7. The pivot connection P7 establishes a pivot axis A7. The pivot connection P7 may be a hinge connecting the pivotable base plate 90 to the angled plate 92 along a width of a side of the angled plate 92 running perpendicular to the view in FIGS. 12 and 13. The base 15 includes a biasing member 80D operatively connected to at least one of the base plate 90 and the angled plate 92 and biasing the base plate 90 to the first position shown in FIG. 12. In the first position, the surface 22A of the base plate 90 is generally parallel with the surface 22 of the base member 16.

When the controller 38 activates the actuator 40 to move the rod 42A, placing the jig 26A into contact with and compressing the cushioning component 12, the downward force of the jig 26A will cause the base plate 90 to pivot to the second position of FIG. 13. The surface 22A of the base plate 90 is then at an angle 95 relative to the position of the surface 22A when the base plate 90 is in the first position. The angle of application of the impact force F1 relative to the support surface 22A changes the angle 95 when the base plate 90 moves from the first position to the second position. In other words, the angle of application of force F1 is at 90 degrees relative to the surface 22A in the first position of FIG. 12, and is at an angle 96 when the base plate 90 is in the second position of FIG. 13, with the angle 96 being 90 degrees less the number of degrees of the angle 95. This may be referred to as a lateral heel strike. Multi-axial deformation of the cushioning component 12 occurs, with shear forces $F_s$, similar to in-use conditions such as during a lateral cutting motion of a basketball player.

Figure 14:
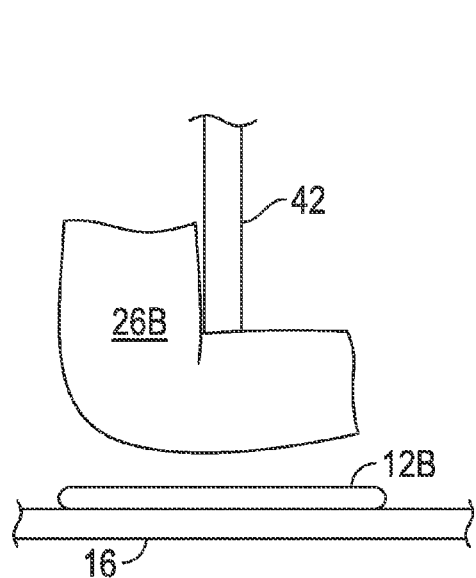
FIG. 14 is a schematic illustration in fragmentary side view of a shoulder-shaped jig spaced from an alternative cushioning component.
Figure 15:
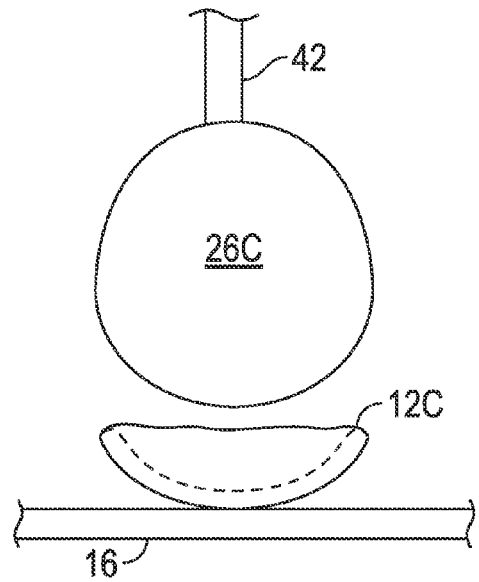
FIG. 15 is a schematic illustration in fragmentary side view of a head-shaped jig spaced from an alternative cushioning component.
Figure 16:
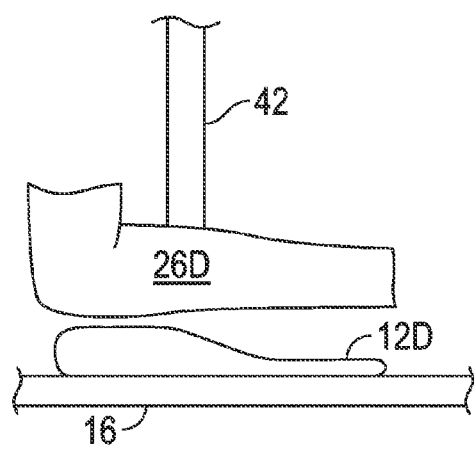
FIG. 16 is a schematic illustration in fragmentary side view of a shin-shaped jig spaced from an alternative cushioning component.
Figure 17:
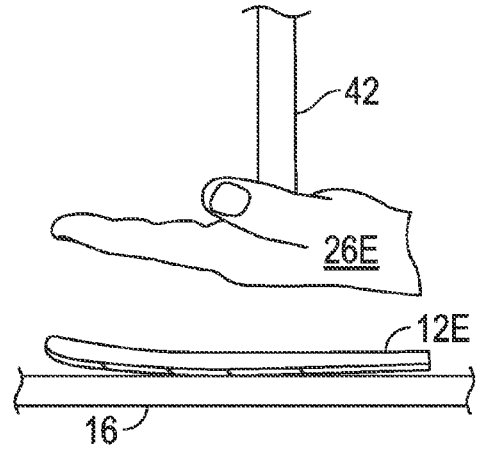
FIG. 17 is a schematic illustration in fragmentary side view of a hand-shaped jig spaced from an alternative cushioning component.
Figure 18:
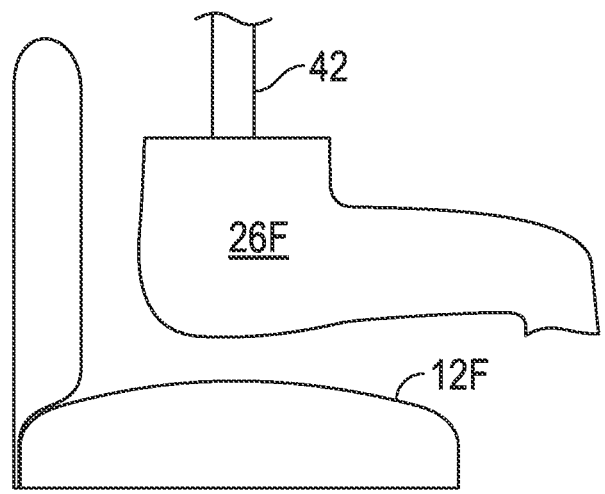
FIG. 18 is a schematic illustration in fragmentary side view of a buttocks-shaped jig spaced from an alternative cushioning component.
Figure 19:
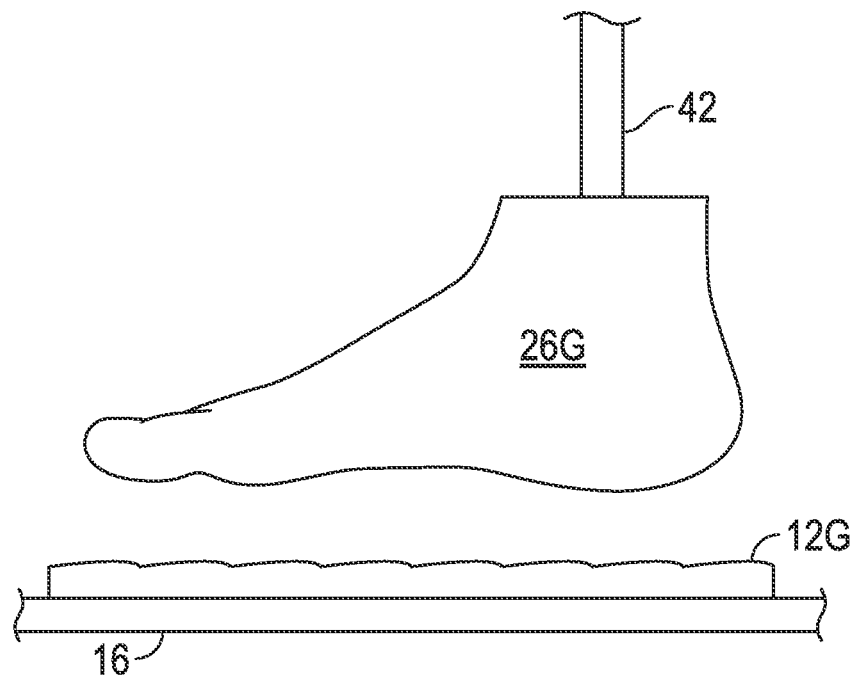
FIG. 19 is a schematic illustration in fragmentary side view of a foot-shaped jig spaced from an alternative cushioning component.

FIGS. 14-19 show various alternative anatomically-shaped jigs that may be used for testing of various different cushioning components. FIG. 14 shows a portion of a shoulder-shaped jig 26B used for testing a cushioning component 12B that is a backpack strap cushion. FIG. 15 shows a head-shaped jig 26C used for testing a cushioning component 12C that is a helmet cushion. FIG. 16 shows a shin-shaped jig 26D that is used for testing a cushioning component 12D that is a shin guard. FIG. 17 shows a hand-shaped jig 26E that is used for testing a cushioning component 12E that is padding for a baseball glove. FIG. 18 shows a buttocks-shaped jig 26F that is used for testing a cushioning component 12F that is a seat cushion. FIG. 19 shows a foot-shaped jig 26G that is used for testing a cushioning component 12G that is a floor mat. Any of the alternative jigs 26B-26G may be used in any of the testing apparatuses 10, 110, 210 in place of jig 26 or 26A to test cushioning components 12B-12G.

Figure 22:
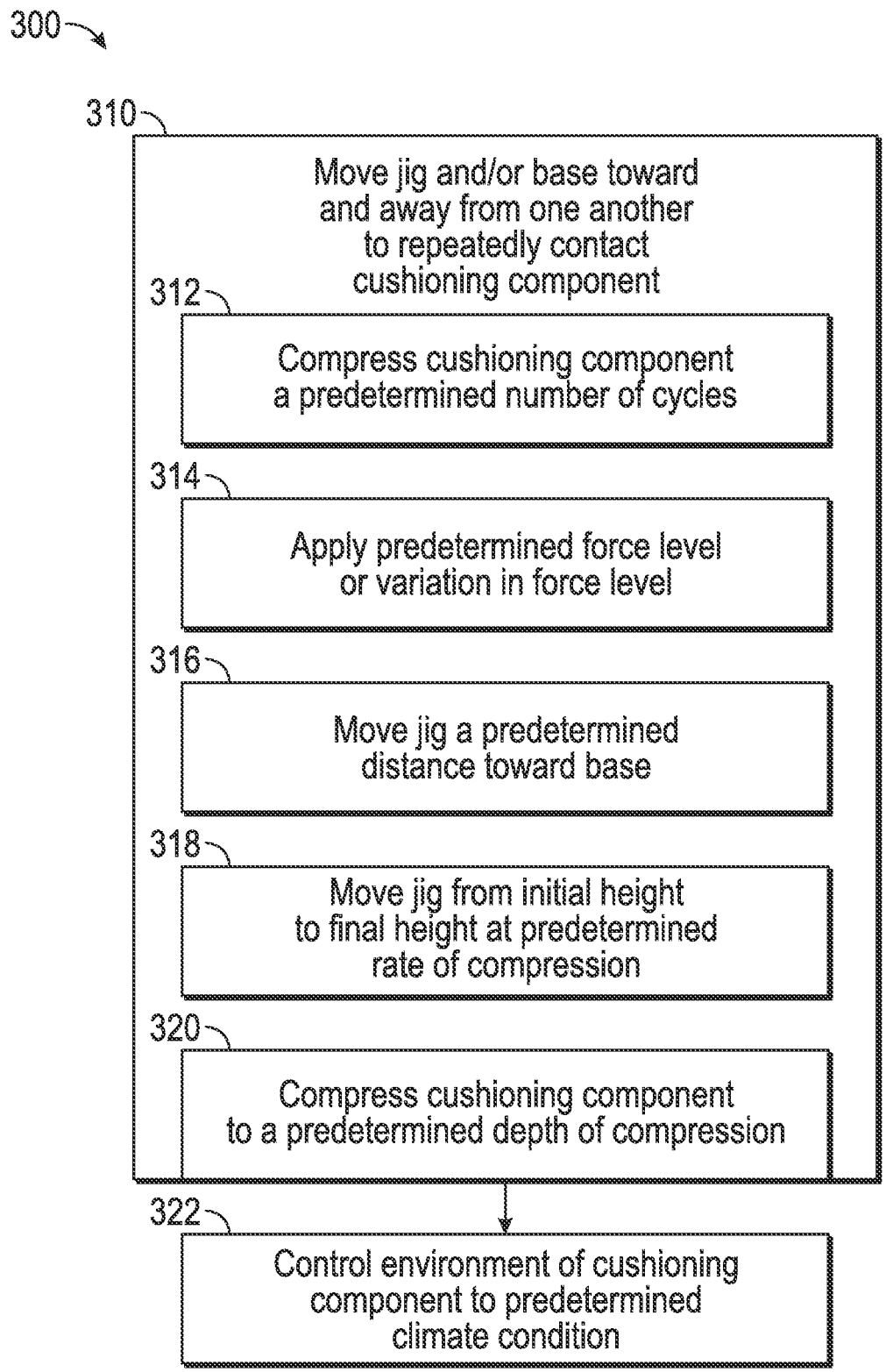
FIG. 22 is a flow chart of a method of testing cushioning components.

As described with respect to FIGS. 1-21 and with reference to FIG. 22, the algorithm 34 implemented by the controller 38 is a method 300 of testing cushioning components 12, 12A-12G that includes step 310, moving at least one of a three-dimensional, anatomically-shaped jig 26, 26A, 26B, 26C, 26D, 26E, 26F, or 26G and a base 15 or 15A toward and away from the other of the jig and the base to repeatedly contact the jig and the cushioning component with one another while the cushioning component is supported on the base. The processor 36 executes the stored algorithm 34, which is a first reliability test having a test condition substantially equivalent to an expected in-use condition of the cushioning component. The method 300 is discussed herein with respect to the apparatus 10, jig 26, base 15, and cushioning component 12, but can be implemented by the controller 38 with any of the apparatuses 10, 110, 210, jigs 26, 26A, 26B, 26C, 26D, 26E, 26F, or 26G; base 15 or 15A; or cushioning components 12, 12A-12G.

Step 310 may include sub-step 312, compressing the cushioning component 12 a predetermined number of cycles with the jig 26. The predetermined number of cycles may be a test condition that represents expected in-use conditions. For example, it may be expected that, in use, the cushioning component 12 will be compressed the predetermined number of times during its expected useful life.

Step 310 may include sub-step 314, compressing the cushioning component 12 by applying a predetermined force level with the jig 26, or a predetermined variation in force levels during the cyclical compressions. The predetermined force level or variation in forces may represent expected in-use conditions, such as the expected force applied by a person of a predetermined foot size and weight.

Step 310 may include sub-step 316, moving the jig 26 toward the base 15 by a predetermined distance D to compress the cushioning component 12 with the jig 26. In this example, one of the test conditions representative of an in-use condition of the cushioning component 12 includes multi-axial forces F acting on the cushioning component 12 and associated with multi-axial deformation of the cushioning component 12 by the jig 26.

Step 310 may also include sub-step 318, moving the jig from an initial height H1 to a final height H2 at a rate resulting in a predetermined rate of compression of the cushioning component 12. In this example, one of the test conditions representative of an in-use condition of the cushioning component 12 includes a predetermined rate of compression of the cushioning component 12.

Optionally, the compression of the cushioning component 12 in step 310 may be controlled in sub-step 320 to be at a predetermined depth of compression that is a function of at least one of a corresponding foot size of the jig 26 and a predetermined force of application of the jig 26 on the cushioning component 12. In this manner, the expected in-use depth of compression of the cushioning component 12 is a test condition of the stored algorithm 34.

Additionally, the method 300 may include step 322, controlling the environment of the cushioning component 12 to a predetermined climate condition. For example, the climate control element 60 can be controlled by the controller 38 to provide a predetermined temperature of the internal space 24, and/or to provide a predetermined humidity of the internal space 24. The predetermined climate condition may be an expected in-use environmental condition of the cushioning component 12 when included in an article of footwear.

Any or all of the test conditions may be selected to provide a failure mode of the cushioning component 12, so that the algorithm 34 accelerates reliability testing of the cushioning component. For example, when the predetermined force F1 is at a predetermined force level, and is applied to create multi-axial forces and shear forces $F_s$ due to the three-dimensional anatomically-shaped jig 26, and optionally, a jig with multiple pivot axes, a loss of expected resiliency of the cushioning component 12 may occur earlier than with a reliability test that is not representative of expected in-use conditions, such as a test that uses a jig that applies only uniaxial forces to the cushioning component 12.

While the best modes for carrying out the disclosure have been described in detail, those familiar with the art to which this disclosure relates will recognize various alternative designs and embodiments for practicing the disclosure within the scope of the appended claims. It is intended that all matter contained in the above description or shown in the accompanying drawings shall be interpreted as illustrative only and not as limiting.

The invention claimed is:

1. An apparatus for testing a cushioning component, the apparatus comprising:
    a jig with a three-dimensional anatomical shape;
    a base configured to support the cushioning component;
    an actuator operatively connected to at least one of the jig and the base, and activatable to move said at least one of the jig and the base toward and away from the other of the jig and the base to repeatedly contact the cushioning component and the jig with one another when the cushioning component is supported on the base;

an electronic controller operatively connected to the actuator; wherein the electronic controller has a processor that executes a stored algorithm; wherein the stored algorithm is a first reliability test having at least one test condition substantially equivalent to an expected in-use condition of the cushioning component; wherein the electronic controller activates the actuator to move said at least one of the jig and the base according to the stored algorithm;

wherein the base includes a pivotable base plate; wherein the pivotable base plate has a support surface on which the cushioning component is supported; wherein the pivotable base plate pivots from a first position to a second position upon compression of the cushioning component by the jig; and wherein an angle of application of the jig relative to the support surface of the base plate on which the cushioning component is supported is different when the base plate is in the first position than when the base plate is in the second position.

2. The apparatus of claim 1, wherein the at least one test condition includes a rate of compression of the cushioning component; and wherein the actuator moves the jig from an initial height to a final height at the rate of compression.

3. The apparatus of claim 2, wherein a difference between the initial height and the final height is a function of at least one of a corresponding size of the jig and a predetermined force of application of the jig on the cushioning component.

4. The apparatus of claim 1, wherein the at least one test condition includes a number of cycles of compressing the cushioning component with the jig.

5. The apparatus of claim 1, further comprising:
a frame supporting the jig and at least partially surrounding the jig and the base to define an internal space;
a climate control element operatively connected to one of the frame and the base;
a gauge operable to measure a climate condition;
wherein the climate control element and the gauge are operatively connected to the electronic controller; wherein the at least one test condition includes a predetermined level of a climate condition; and wherein the stored algorithm includes maintaining the internal space at the predetermined level of the climate condition by controlling the climate control element.

6. The apparatus of claim 5, wherein the climate condition is one of temperature and humidity.

7. The apparatus of claim 1, wherein the three-dimensional anatomical shape is a shape substantially identical to a human body part.

8. The apparatus of claim 7, wherein the anatomical shape is any one of a foot shape, a shoulder shape, a knee shape, a hand shape, a head shape, and a buttocks shape.

9. The apparatus of claim 1, wherein the at least one test condition includes multi-axial deformation of the cushioning component associated with compressing the cushioning component with the jig; and wherein the multi-axial deformation causes transverse shear stresses in the cushioning component.

10. The apparatus of claim 9, further comprising:
a rod pivotably connected to the jig and movable by the actuator to move the jig into contact with the cushioning component, the jig thereby pivoting relative to the rod in response to contact with the cushioning component;
wherein the three-dimensional anatomical shape of the jig is a foot shape having a heel portion and a forefoot portion; and wherein the rod is connected to the jig closer to the heel portion than the forefoot portion.

11. The apparatus of claim 10, further comprising:
a biasing member connected at a first end to the rod and connected at a second end to the forefoot portion of the jig and biasing the jig to a first position relative to the rod;
wherein the jig pivots from the first position to a second position relative to the rod upon compression of the cushioning component; and wherein the biasing member returns the jig to the first position when the actuator moves the jig away from the base, out of contact with the cushioning component.

12. The apparatus of claim 9, further comprising:
a rod pivotably connected to the jig and movable by the actuator to move the jig into contact with the cushioning component to compress the cushioning component;
a first biasing member pivotably connecting the rod to a first side of the jig; and
a second biasing member pivotably connecting the rod to a second side of the jig; the jig thereby being pivotable relative to the rod toward either the first side or the second side in response to the jig compressing the cushioning component.

13. The apparatus of claim 1, wherein the base includes an angled plate; wherein the pivotable base plate is pivotably connected to the angled plate between the jig and the angled plate; and
wherein the base includes a biasing member operatively connected to at least one of the base plate and the angled plate and biasing the base plate to the first position.

14. The apparatus of claim 13, further comprising:
a rod pivotably connected to the jig and movable by the actuator to move the jig into contact with the cushioning component to compress the cushioning component;
wherein the three-dimensional anatomical shape of the jig is a foot shape having a heel portion; wherein the rod is connected to the jig such that the cushioning component is compressed by the heel portion;
a first biasing member connecting the rod to a lateral side of the jig;
a second biasing member connecting the rod to a medial side of the jig; the jig thereby being pivotable relative to the rod toward either the medial side or the lateral side, from an unpivoted position to a pivoted position, in response to contact with the cushioning component and pivoting of the base plate when the jig compresses the cushioning component; and
wherein the biasing members return the jig to the unpivoted position when the jig is moved out of contact with the cushioning component.

15. A method of testing cushioning components comprising:
moving at least one of a three-dimensional, anatomically-shaped jig and a base toward and away from the other of the jig and the base to repeatedly contact the jig and a cushioning component supported on the base with one another to compress the cushioning component by the jig;
wherein the base includes a pivotable base plate; wherein the pivotable base plate has a support surface on which the cushioning component is supported; wherein the pivotable base plate pivots from a first position to a second position upon compression of the cushioning component with the jig;

wherein an angle of application of the jig relative to the support surface of the base plate on which the cushioning component is supported is different when the base plate is in the first position than when the base plate is in the second position;

wherein said moving is by executing an algorithm stored in a processor of an electronic controller to activate an actuator that moves said at least one of the jig and the base;

wherein the stored algorithm is a first reliability test and wherein pivoting from the first position to the second position upon compression of the cushioning component with the jig is a test condition substantially equivalent to an expected in-use condition of the cushioning component.

16. The method of claim 15, wherein at least one test condition of the reliability test includes any of:

multi-axial forces acting on the cushioning component and associated with multi-axial deformation of the cushioning component by the jig;

a rate of compression of the cushioning component; wherein the jig is moved from an initial height to a final height at the rate of compression;

a number of cycles of compressing the cushioning component with the jig; or a depth of compression of the cushioning component by the jig; wherein the depth of compression is a function of at least one of a corresponding foot size of the jig and a predetermined force of application of the jig on the cushioning component.

17. The method of claim 15, wherein at least one test condition of the reliability test includes a predetermined level of a climate condition of an environment of the cushioning component; and further comprising:

controlling the environment of the cushioning component to the predetermined level of the climate condition.

18. The method of claim 15, wherein the algorithm is executed by the controller until the occurrence of a failure mode of the cushioning component; and wherein the failure mode is accelerated with the test condition.

19. The method of claim 15, wherein said moving comprises moving the jig a predetermined distance to compress the cushioning component with the jig.

20. An apparatus for testing a cushioning component, the apparatus comprising:

a jig with a three-dimensional anatomical shape;

a base configured to support the cushioning component;

an actuator operatively connected to at least one of the jig and the base, and activatable to move said at least one of the jig and the base toward and away from the other of the jig and the base to repeatedly contact the cushioning component and the jig with one another when the cushioning component is supported on the base;

an electronic controller operatively connected to the actuator; wherein the electronic controller has a processor that executes a stored algorithm; wherein the stored algorithm is a first reliability test having at least one test condition substantially equivalent to an expected in-use condition of the cushioning component; wherein the electronic controller activates the actuator to move said at least one of the jig and the base according to the stored algorithm;

a rod pivotably connected to the jig and movable by the actuator to move the jig into contact with the cushioning component, the jig thereby pivoting relative to the rod in response to contact with the cushioning component;

a biasing member connected at a first end to the rod and connected at a second end to the jig and biasing the jig to a first position relative to the rod; wherein the jig pivots from the first position to a second position relative to the rod upon compression of the cushioning component; and wherein the biasing member returns the jig to the first position when the actuator moves the jig away from the base, out of contact with the cushioning component.

* * * * *